United States Patent [19]

Brown et al.

[11] Patent Number: 4,857,651
[45] Date of Patent: Aug. 15, 1989

[54] α-(2,3-DI(C$_1$–C$_4$ ALKOXY)ETHYLAMINO)-β-CYANOSTYRENE AND β-NITROSTYRENE COMPOUNDS USEFUL AS INTERMEDIATES IN THE PREPARATION OF INSECTICIDAL, ACARICIDAL AND NEMATICIDAL ARYLPYRROLES AND METHOD FOR THE PREPARATION THEREOF

[75] Inventors: Dale G. Brown, Hunterdon; Jack K. Siddens, Princeton Junction; Robert E. Diehl, Lawrenceville; Donald P. Wright, Jr., Pennington, all of N.J.

[73] Assignee: American Cyanamid Company, Stamford, Conn.

[21] Appl. No.: 79,543

[22] Filed: Jul. 29, 1987

[51] Int. Cl.$^4$ .......................................... C07D 317/44
[52] U.S. Cl. ................................. 549/443; 549/442; 549/511; 558/401; 558/403; 558/408; 564/384

[58] Field of Search ............... 558/401, 403, 408; 564/384; 549/443, 511, 442

[56] References Cited

U.S. PATENT DOCUMENTS

| | | | |
|---|---|---|---|
| 3,341,541 | 9/1967 | Hoffer | 558/401 X |
| 3,341,584 | 9/1967 | Larsen et al. | 549/443 X |
| 4,167,580 | 9/1979 | Sloboda | 558/401 X |
| 4,681,970 | 7/1987 | Liang | 558/408 |

*Primary Examiner*—Patrick P. Garvin
*Assistant Examiner*—George R. Fourson
*Attorney, Agent, or Firm*—Alice C. Brennan

[57] ABSTRACT

This invention provides novel α-[2,2-di(C$_1$–C$_4$ alkoxy)ethylamino]-β-cyanostyrene and α-[2,2-di(C$_1$–C$_4$ alkoxy)ethylamino]-β-nitrostyrene compounds that are useful for the preparation of pesticidal arylpyrroles. The invention also provides a method for the preparation of the above-said β-cyanostyrene and β-nitrostyrene compounds.

16 Claims, No Drawings

α-(2,3-DI(C₁-C₄ ALKOXY)ETHYLAMINO)-β-CYANOSTYRENE AND β-NITROSTYRENE COMPOUNDS USEFUL AS INTERMEDIATES IN THE PREPARATION OF INSECTICIDAL, ACARICIDAL AND NEMATICIDAL ARYLPYRROLES AND METHOD FOR THE PREPARATION THEREOF

SUMMARY OF THE INVENTION

The present invention provides novel α-[2,2-di($C_1$-$C_4$ alkoxy)ethylamino]-β-cyano- and nitrostyrene compounds useful as intermediates in the preparation of insecticidal, acaricidal and nematicidal arylpyrroles and a method for the preparation of said β-cyanostyrene and β-nitrostyrene compounds.

The insecticidal, acaricidal and nematicidal arylpyrroles referred to above are described in the copending United States Patent Application of D. G. Brown, J. K. Siddens, R. E. Diehl and D. P. Wright, Jr., Ser. No. 208,841, filed June 23, 1988 and incorporated herein by reference thereto.

DETAILED DESCRIPTION OF THE INVENTION

The α-[2,2-di($C_1$-$C_4$ alkoxy)ethylamino]-β-cyanostyrene and α-[2,2-di($C_1$-$C_4$ alkoxy)ethylamino]-β-nitrostyrene compounds of this invention are depicted by the following structural formula:

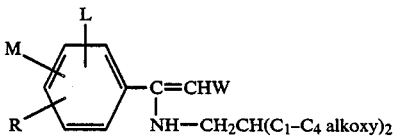

wherein W is CN or $NO_2$; L is H, F, Cl or Br; M and R are each independently H, $C_1$-$C_3$ alkyl, $C_1$-$C_3$ alkoxy, $C_1$-$C_3$ alkylthio, $C_1$-$C_3$ alkylsulfinyl, $C_1$-$C_3$ alkylsulfonyl, cyano, F, Cl, Br, I, nitro, $CF_3$, $R_1CF_2Z$, $R_2CO$, or $NR_3R_4$ and when on adjacent positions and taken together with the carbon atoms to which they are attached M and R may form a ring in which MR represent the structure: —$OCH_2$)—, —$OCF_2O$—

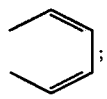

;

Z is S(O)n or O; $R_1$ is H, F, $CHF_2$, CHFCl, or $CF_3$; $R_2$ is $C_1$-$C_3$ alkyl, $C_1$-$C_3$ alkoxy, or $NR_3R_4$; $R_3$ is H or $C_1$-$C_3$ alkyl; $R_4$ is H, $C_1$-$C_3$ alkyl or $R_5CO$; $R_5$ is H or $C_1$-$C_3$ alkyl; and n is an integer of 0, 1 or 2.

A preferred group of β-(substituted)styrene compounds of the present invention have the above-illustrated structure wherein W is CN; L is H, Cl or Br; M is H, F, Cl, Br or $OCH_3$; R is H, F, Cl, Br, $CF_3$, $NO_2$, $OCF_3$ or $OCH_3$; or when on adjacent positions and taken together with the carbon atoms to which they are attached M and R may form a ring in which MR represents the structure:

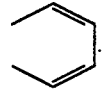

Another preferred group of β-(substituted)styrene compounds of this invention have the above-illustrated structure wherein W is $NO_2$; L is H, Cl or Br; M is H, F, Cl, Br or $OCH_3$; R is H, F, Cl, Br, $CF_3$, $NO_2$, $OCF_3$; or $OCH_3$; or when on adjacent positions and taken together with the carbon atoms to which they are attached M and R may form a ring in which MR represents the structure:

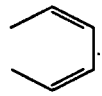

While the compounds of the present invention are referred to above as β-cyanostyrenes and β-nitrostyrenes, they may also be named as dialkyl acetals.

Some of the preferred dialkyl acetal compounds of this invention are (E) and (Z) (1)p-chloro-β-[(formylmethyl)amino]cinnamonitrile diethyl acetal; (2)β-[(formylmethyl)amino]-3,4-dimethoxycinnamonitrile diethyl acetal; (3)(Z)-methyl p-{2-cyano-1-[(formylmethyl)amino]vinyl}benzoate diethyl acetal; (4)(Z)-β-[(formylmethyl)amino]-1-naphthaleneacrylonitrile diethyl acetal; (5)(Z)-β-[(formylmethyl)amino]-p-methylcinnamonitrile diethyl acetal; (6)N-(formylmethyl)-p-methyl-α-(nitromethylene)benzylamine diethyl acetal; (7)N-(formylmethyl)-3,4-dimethoxy-α-(nitromethylene)benzylamine diethyl acetal; (8)N-(formylmethyl)-α-(nitromethylene)-2-naphthalenemethylamine diethyl acetal; (9)methyl p-{α-[(formylmethyl)amino]-β-nitrovinyl}benzoate p-(diethyl acetal); (10)N-(formylmethyl)-3,4-dimethoxy-α-(nitromethylene)benzylamine dimethyl acetal; (11)(E) and (Z) p-chloro-β-[(formylmethyl)amino]cinnamonitrile dimethyl acetal; (12)β-[(formylmethyl)amino]-3,4-dimethoxycinnamonitrile dimethyl acetal; (13)3,4-dichloro-β-[(formylmethyl)amino]-cinnamonitrile diethyl acetal; and (14)p-trifluoromethyl-β-[(formylmethyl)amino]cinnamonitrile diethyl acetal.

The β-cyanostyrenes, also referred to as cinnamonitrile dialkyl acetals, can be prepared by the reaction of a substituted or unsubstituted benzoyl acetonitrile with a 2,2-di($C_1$-$C_4$ alkoxy)ethylamine in the presence of an aromatic solvent to form the α-(2,2-di($C_1$-$C_4$ alkoxy)ethylamino)-β-cyano-(substituted)styrene which then may be converted to a 2-(substituted-phenyl)pyrrole-3-carbonitrile by reaction of said β-3-cyano(substituted)styrene compound with trifluoroacetic acid. Chlorination of the thus prepared cyanophenyl pyrrole with sodium hypochlorite or sulfuryl chloride in an inert solvent yields the insecticidal, acaricidal, and nematicidal 4,5-dichloro-2-(substituted-phenyl) pyrrole-3-carbonitrile. The conversion to the pyrrole intermediate may also be achieved by substituting concentrated HCl at a temperature between about 20° and 40° C. The reactions may be graphically illustrated as follows:

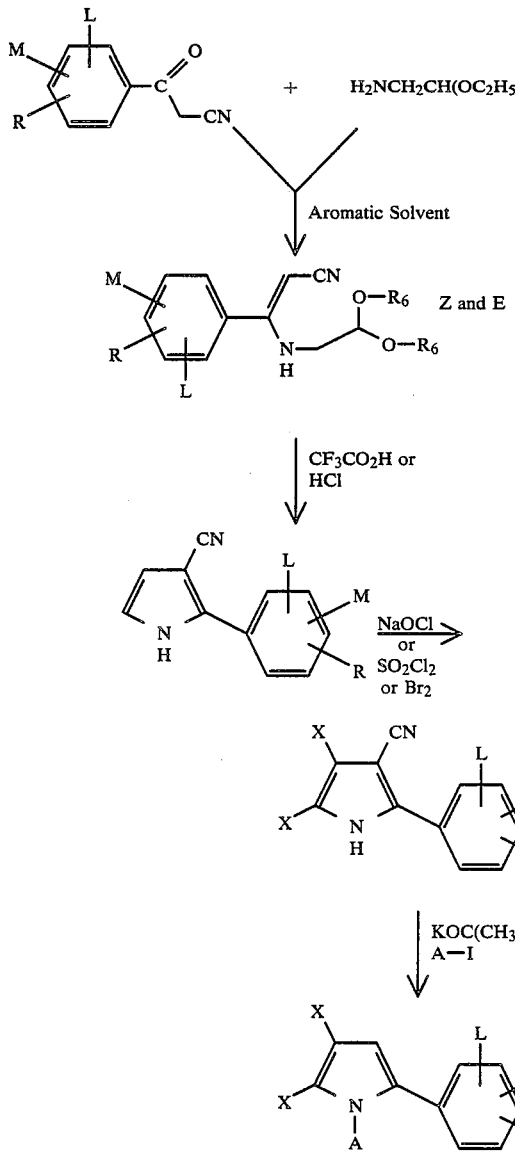

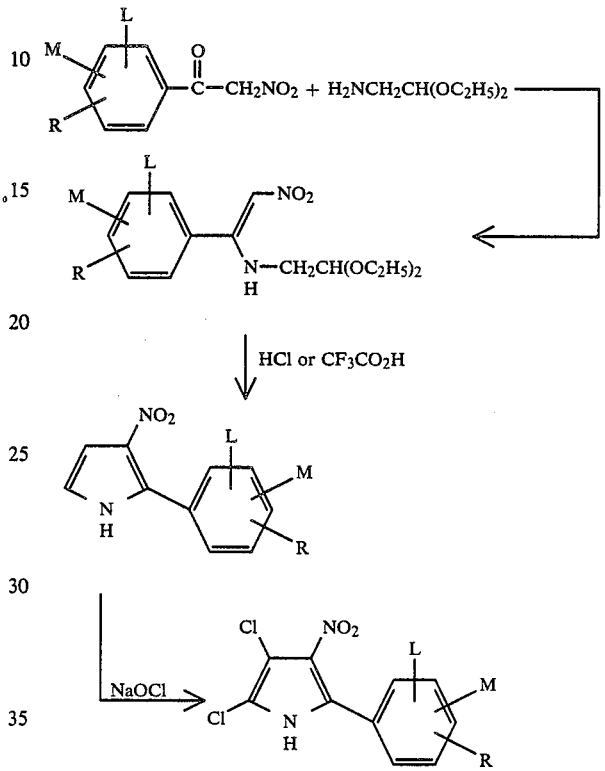

wherein A is hydrogen, $C_1$-$C_4$ alkyl optionally substituted with one $C_1$-$C_4$ alkoxy, one $C_1$-$C_4$ alkylthio, from one to three halogen groups, or phenyl optionally substituted with one or two $C_1$-$C_4$ alkyl, $C_1$-$C_4$ alkoxy, or halogen groups; $C_3$-$C_4$ alkenyl optionally substituted with from to three halogen groups; or $C_3$-$C_4$ alkynyl; X is Cl or Br; $R_6$ is $C_1$-$C_4$ alkyl and L, R and M are as described above.

Also in accordance with the present invention the biologically active 3-nitro-2-phenylpyrrole and 3-nitro-2-(substituted)phenylpyrrole compounds can be prepared by reaction of an α-nitroacetophenone or a substituted α-nitroacetophenone with a 2,2-di($C_1$-$C_4$-alkoxy)ethylamine to give the β-nitrostyrene compounds of this invention. The reaction is generally conducted in the presence of an inert organic solvent preferably an aromatic solvent, at an elevated temperature and gives an α-(2,2-di($C_1$-$C_4$-alkoxy)ethylamino)-β-nitrostyrene or a substituted α-(2,2-di($C_1$-$C_4$-alkoxy)ethylamino)-β-nitrostyrene that is readily converted to the active 3-nitro-2-phenylpyrrole or 3-nitro-2-(substituted)phenylpyrrole by treatment with a mineral acid such as hydrochloric or hydrobromic acid. Reaction of the thus prepared nitrophenylpyrrole with sodium hypochlorite in the presence of an inert organic solvent at a reduced temperature yields the 2,3-dichloro-4-nitro-5-phenyl or 5-(substituted)phenylpyrrole.

The above reactions may be graphically illustrated as follows:

In addition to the several methods described in the literature for preparing substituted and unsubstituted benzoyl acetonitriles, which are starting materials for the preparation of the β-cyanostyrenes of this invention, surprisingly we have found that these compounds may also be prepared by reacting an appropriately substituted benzoyl halide with an alkali metal hydride and an alkyl cyanoacetate, such as t-butyl cyanoacetate, to yield the corresponding t-butyl(benzoyl or substituted benzoyl)cyanoacetate. These reactions may be graphically illustrated as follows:

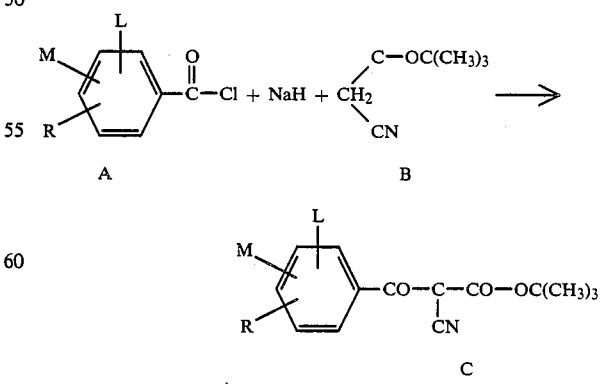

The thus formed cyanoacetate ester can then be converted to a substituted or unsubstituted benzoyl acetonitrile by heating the compound in toluene containing p-toluene sulfonic acid. The reaction may be graphically illustrated as follows:

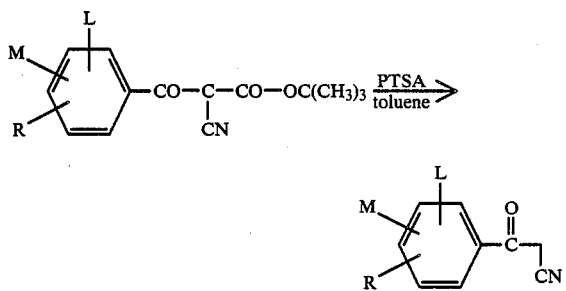

Examples of the t-butyl(benzoyl and substituted benzoyl)-cyanoacetates are illustrated below.

t-Butyl (benzoyl and Substituted benzoyl)cyanoacetates

| L | M | R | mp °C. |
|---|---|---|---|
| H | 3-Cl | 4-Cl | 91–94 |
| H | H | 4-OCF$_3$ | 81–84 |
| H | H | 4-Br | 113–115 |
| H | H | 4-CF$_3$ | 146–147 |
| H | H | 4-F | 98–100 |
| H | H | 4-CN | 127–128 |
| H | H | 4-CF$_3$CH$_2$O | 136–139 |
| H | H | 4-CH$_3$SO$_2$ | 127–129 |
| H | 3-F | 4-F | 91–94 |
| H | H | 4-CH$_3$S | 117–119.5 |
| H | H | 4-CHF$_2$CF$_2$O | 92–94 |
| 3-Cl | 5-Cl | 4-CH$_3$O | — |

Benzoyl Acetonitriles

| L | M | R | mp °C. |
|---|---|---|---|
| H | H | 4-Cl | 128.5–129.5 |
| H | 3-Cl | 4-Cl | 105–107 |
| H | H | 2-Cl | 53–55 |
| H | H | 4-OCF$_3$ | 79–81 |
| H | H | 4-CF$_3$ | 44–45 |
| H | 2-Cl | 4-Cl | 66–67 |
| H | H | 3-Cl | 80–83 |
| H | H | 4-CN | 126–128 |
| H | H | 4-F | 78–80 |
| H | H | 4-SO$_2$CH$_3$ | 129–132 |
| H | 3-F | 4-F | 74–75 |
| H | H | 3-CF$_3$ | 58–60 |
| H | H | 4-CH$_3$ | 103.5–106 |
| H | H | 4-NO$_2$ | 119–124 |
| 3-Cl | 5-Cl | 4-OCH$_3$ | — |

The 2-aryl-3-cyano-4,5-dihalopyrroles prepared from the β-cyano-styrene compounds of the present invention are effective for controlling insects, acarina and nematodes. These compounds are also effective for protecting growing or harvested crops from attack by the above-said pests.

In practice generally about 10 ppm to 10,000 ppm and preferably 100 to 5000 ppm, of the halogenated arylpyrrole dispersed in water or other inexpensive liquid carrier is effective when applied to the plants, the crops or the soil in which said crops are growing to protect said crops from attack by insects, acarina and/or nematodes.

The above-said halogenated arylpyrroles are also effective for controlling insects, nematodes and acarina, when applied to the foliage of plants and/or to the soil or water in which said plants are growing. These halogenated arylpyrrole compounds are usually applied in sufficient amount to provide a rate of from about 0.125 kg/ha to about 4.0 kg/ha of active ingredient. Obviously higher rates of application of said halogenated arylpyrroles may be used to protect crops from attack by insects, nematodes and acarina, however, higher rates of application are generally unnecessary and wasteful.

Advantageously, the above-said arylpyrroles may be formulated into dry compacted granules, flowable compositions, granular formulations, wettable powders, emulsifiable concentrates, dusts, dust concentrates, microemulsions and the like, all of which lend themselves to soil, water and/or foliage application and provide the requisite plant protection. Such formulations include the compounds of the invention admixed with inert, pharmacologically- acceptable solid or liquid diluents.

For example, wettable powders, dusts and dust concentrate formulations of the invention can be prepared by grinding together about 3% to 20%, by weight, of the formula I arylpyrrole compound, with about 3% to 20% by weight of a solid anionic surfactant. One suitable anionic surfactant is a dioctyl ester of sodium sulfosuccinic acid, specifically Aerosol OTB ® surfactant marketed by the American Cyanamid Company. About 60% to 94%, by weight, of an inert solid diluent, such as montmorillonite, attapulgite, chalk, talc, kaolin, diatomaceous earth, limestone, silicates or the like also is used in such formulations.

Compacted granules especially useful for soil or water application can be prepared by grinding together in about equal parts, usually about 3 to 20 parts, of the arylpyrrole and a solid surfactant, with about 60 to 94 parts of gypsum. Thereafter, the mixture is compacted into small granular particles, about 24/48 mesh or larger.

Other suitable solid surfactants useful in the present formulations include not only the anionic dioctyl ester of sodium sulfosuccinic acid but also nonionic block copolymers of ethylene oxide and propylene oxide. Such block copolymers are marketed by BASF Wyandotte Corporation as Pluronic 10R8 ®, 17R8 ®, 25R8 ®, F38 ®, F68 ®, F77 ® or F87 ®, and are especially effective for the preparation of compacted granules In addition to the powders and concentrate formulations described hereinabove, wettable powders and flowables may be used because they may be dispersed in water. Preferably, such flowables will be applied at the locus with the aqueous compositions being sprayed on the foliage of plants to be protected. These sprays also may be applied to the breeding ground, food supply or habitat of the insects and acarina sought to be controlled.

Where solid formulations of the arylpyrroles are to be used in combination treatments with other pesticidal agents, the formulations can be applied as an admixture of the components or may be applied sequentially.

Similarly, liquid formulations of the arylpyrrole in combination with other pesticidal agents may be tank mixed or may be applied separately, sequentially, as liquid sprays. Liquid spray formulations of the compounds of the invention should contain about 0.001% to 0.1% by weight of the active arylpyrrole.

The following examples are presented as illustrations of the present invention.

EXAMPLE 1 p-chloro-β-[(formylmethyl)amino]cinnamonitrile, diethyl acetal

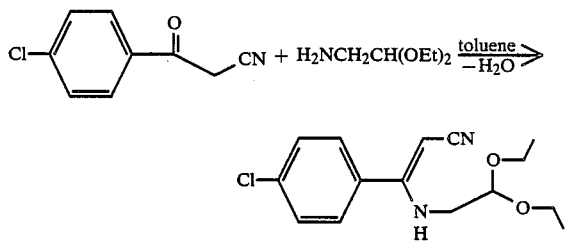

A magnetically stirred solution of 250.0 g (1.39 mol,) of p-chlorobenzoylacetonitrile, 203 mL (185.9 g, 1.39mol) of 2,2-diethoxyethylamine, and 1300 mL of dried toluene is heated at reflux for 20 hours. Water is collected in a Dean-Stark trap (23.8 mL, 95.2% theory). The hot cloudy dark brown solution with a large amount of undissolved solids is filtered through diatomaceous filter aid. After dilution with 200 mL of EtOAc, the solution is filtered through a 7cm×13.5cm column of silica gel. The filtrate is concentrated in vacuo to give 354.3 g (86.4% crude yield) of a clear dark oil which slowly solidifies. This solid is recrystallized from hot cyclohexane to give 324.2 g (79.1% yield) of a waxy orange solid. NMR of this product shows it to be composed of 78% (Z) and 23% (E) isomeric mixture of p-chloro-β-[(formylmethyl)amino]cinnamonitrile, diethyl acetal, m.p. 60°-72° C. The following analytical data is for another similarly prepared sample. Max(mull,Nujol): 3325(s), 3065(m), 2197(s), 1600(s), 1530(s), 1314(m), 1265(m), 1173(m), 1154(m), 1128(s), 1100(s), 1060(s), 1022(s), 939 (m), 895(m), 844(s), 768(m), 730(m) Cm$^{-1}$.

H-NMR(chloroform): δ7.47 (d, J=8.6Hz, 2.12H, two aromatic protons), δ7.37 (d, J=8.6Hz, 2.1H, two aromatic protons), δ5.10(E) & δ4.86(Z) [br t, 1.25H, one N-H proton], δ4.69(Z) & δ4.60(E) [t, J=5.1Hz, 1.05H, one mehtine proton at the acetal carbon], δ4.07 (E) & δ4.05(Z) [s, 0.8H, enamine β proton], δ3.71(E) & δ3.68(Z) [q, J=7.1Hz, 2.22H, two methylene protons of one of two ethoxy groups], δ3.56(Z) & δ3.53(E) [q, J=7.1Hz, 2.22H, two methylene protons of one of two ethoxy groups], δ3.18 (t, J=5.1Hz, 1.77H, two methylene protons of the ethyleneacetal group), δ1.20 (t, J=7.1Hz, 4.9OH, six methyl protons of the two ethoxy groups).

C-NMR(chloroform): δ161.21 (α-enamine carbon), δ136.29 (Z) & δ134.60(E) [either C-1 or C-4 of the phenyl ring,], δ134.08(Z) & δ132.30(E) [either C-1 or C-4 of the phenyl ring], δ129.34(Z) & δ129.89(E) [either C-2, 6 or C-3,5 of the phenyl ring], δ128.94(Z) & δ128.63(E) [either C-2, 6 or C-3,5 of the phenyl ring], δ121.19(Z) & δ119.50(E) [nitrile carbon], δ99.43(Z) & δ100.63(E) [δ-enamine carbon], δ61.88(Z) & δ63.25(E) [methine carbon of the acetal], δ62.64(Z) & δ63.03(E) [methylene carbons of the ethoxy groups], δ46.32(Z) & δ47.33(E) [methylene carbon of the ethyl amine group], δ15.26 (methyl carbons of the ethoxy groups).

Microanalysis (MW 294.78):
Calcd: C, 61.11%; H, 6.50%; N, 9.51%; Cl, 12.03%.
Found: C, 61.25%; H, 6.25%; N, 9.34%; Cl, 12.35%.

Following the above procedure but substituting the appropriate benzoylacetoylacetonitrile for p-chlorobenzoylacetonitrile and/or the appropriate 2,2-di(C$_1$-C$_4$ alkoxy)ethylamine for 2,2-diethoxyethylamine yields the following compounds:

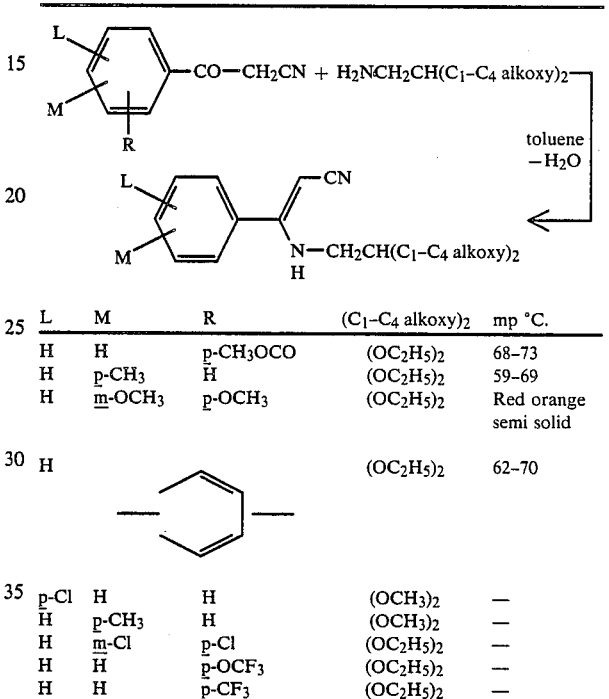

| L | M | R | (C$_1$-C$_4$ alkoxy)$_2$ | mp °C. |
|---|---|---|---|---|
| H | H | p-CH$_3$OCO | (OC$_2$H$_5$)$_2$ | 68–73 |
| H | p-CH$_3$ | H | (OC$_2$H$_5$)$_2$ | 59–69 |
| H | m-OCH$_3$ | p-OCH$_3$ | (OC$_2$H$_5$)$_2$ | Red orange semi solid |
| H | (fused benzene) | | (OC$_2$H$_5$)$_2$ | 62–70 |
| p-Cl | H | H | (OCH$_3$)$_2$ | — |
| H | p-CH$_3$ | H | (OCH$_3$)$_2$ | — |
| H | m-Cl | p-Cl | (OC$_2$H$_5$)$_2$ | — |
| H | H | p-OCF$_3$ | (OC$_2$H$_5$)$_2$ | — |
| H | H | p-CF$_3$ | (OC$_2$H$_5$)$_2$ | — |

EXAMPLE 2

2(p-chlorophenyl)-pyrrole-3-carbonitrile

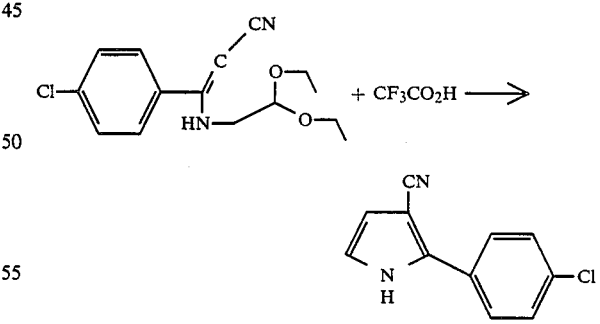

To 108 mL of trifluoroacetic acid stirred at 23° C. is added 54.00 g (0.183mol) of solid p-chloro-β-[(formylmethyl)amino]cinnamonitrile, diethyl acetal over a period of 45 minutes. This addition produced an exotherm to 38° C. and, 32 minutes into the addition, a solid started to precipitate. After stirring at room temperature for 30 minutes, the reaction mixture is vacuum filtered and the collected solid is washed first with trifluoroacetic acid, secondly with an ethyl acetate-hexane mixture, and finally with hexane. The yield is 16.83 g (45.4%) of an off-white solid, mp 165°–166° C. The following anal. data is from a similarly prepared sample.

Max(mull, Nujol): 3275(br s), 2225(s), 1502(s), 1410(m), 1275(m), 1200(m), 1108(s), 1023(m), 999(m), 908(m), 843(s), 752(s), 722(s), 695(s), 620(s) Cm$^{-1}$.

H-NMR(acetone): $\delta$11.22 (v br s, 0.99H, one pyrrole N—H proton), $\delta$7.82 d, J=8.9Hz, 2.46H, two aromatic phenyl protons), $\delta$7.51 (d, J=8.9Hz, 2.46HZ, two aromatic phenyl protons), $\delta$7.02 (t, J=2.6Hz, 1.01H, one pyrrole proton at C-5), $\delta$6.58 (t, J=2.6Hz, 0.77H, one pyrrole proton at C-4).

C-NMR(acetone): $\delta$137.73 (pyrrole C=2), $\delta$134.42 (p-chlorophenyl at C-4), $\delta$129.93 (methine carbons at C-3,5 of the phenyl ring), $\delta$128.07 (methine carbons at C-2,6 of the phenyl ring), $\delta$121.21 (pyrrole at C-5), $\delta$117.93 nitrile carbon), $\delta$113.78 (pyrrole carbon at C-4), $\delta$90.86 (pyrrole carbon at C-3).

Microanalysis (MW 202.64):
Calcd.: C, 65.19%; H, 3.48%; N, 13.83%; Cl, 17.50%.
Found: C, 64.18%; H, 3.52%; N, 13.63%; Cl, 17.74%.

Use of the above procedure as shown or with the substitution of concentrated hydrochloric acid for trifluoroacetic acid affords the following compounds:

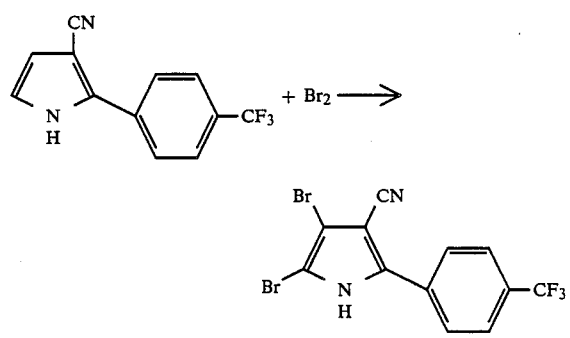

| M and/or R | mp °C. | Acid Used |
|---|---|---|
| 4-Cl | 165–166 | conc. HCl, CF$_3$COOH |
| 3,4-di-Cl | 216–221 | CF$_3$COOH |
| 2-Cl | 156–157 | CF$_3$COOH |
| 4-OCF$_3$ | 143–145 | CF$_3$COOH |
| 4-CF$_3$ | 179–180 | CF$_3$COOH |
| 2,4-di-Cl | 197–199 | CF$_3$COOH |
| 3-Cl | 150–156 | CF$_3$COOH |
| 4-CN | 210–212 | CF$_3$COOH |
| 4-F | 167–170 | conc. HCl |
| 4-SO$_2$CH$_3$ | 221–221.5 | CF$_3$COOH |
| 3,4-di-F | 173–175.5 | CF$_3$COOH |
| 3-CF$_3$ | 166–168 | CF$_3$COOH |
| 4-COOCH$_3$ | 155.5–158 | CF$_3$COOH |
| 4-CH$_3$ | 117–137 | CF$_3$COOH |
| 4-NO$_2$ | 174–177 | CF$_3$COOH |

EXAMPLE 3

4,5-Dichloro-2-(p-chlorophenyl)pyrrole-3-carbonitrile

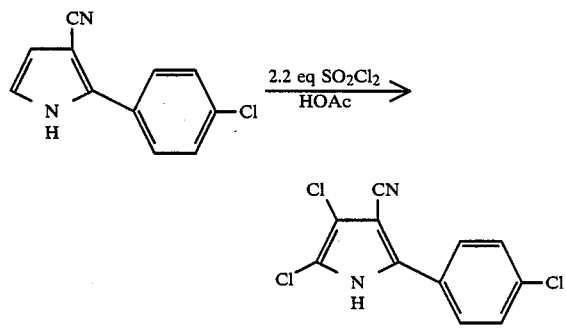

To a mechanically stirred solution of 16.83 g (83.1 mmol) of 2-(p-chlorophenyl)pyrrole-3-carbonitrile in 450 ml of glacial acetic acid at 36° C. is added dropwise 14.7 mL (24.70 g, 183.0 mmol) of sulfuryl chloride over a period of 18 minutes. The addition produces a slight exotherm to 39° C. and, after another 16 minutes, the reaction mixture is vacuum filtered. The collected solids are washed first with acetic acid and then with water. This solid after recrystallization from hot ethyl acetate, melts at 259°–261° C. By similar procedures other samples of this product were prepared and the analytical data for one such product is shown below.

Max(mull, Nujol): 3170(br s), 3100(m), 2225(s), 1508(m), 1097(m), 825(s), 717(m), 660(m) cm$^{-1}$.

H-NMR(DMSO): $\delta$7.72 (d, J=8.6Hz, 2.00H, two aromatic protons), $\delta$7.56 (d, J=8.6Hz, 2.00H, two aromatic protons).

C-NMR(DMSO): $\delta$136.01 (pyrrole C-2 carbon), $\delta$133.92 (p-chlorophenyl C-4 carbon), $\delta$129.09 (p-chlorophenyl C-3,5 carbons), $\delta$127.41 (p-chlorophenyl C-4 carbon), $\delta$127.11 (p-chlorophenyl C-1 carbon), $\delta$114.49 (nitrile carbon), $\delta$114.10 (pyrrole C-5 carbon), $\delta$110.92 (pyrrole C-4 carbon), $\delta$90.09 (pyrrole C-3 carbon).

Microanalysis (MW 271.54):
Calcd.: C, 48.65%, H, 1.86%; N, 10.32%; Cl, 39.17%.
Found: C, 49.22%; H, 2.12%; N, 9.85%; Cl, 39.03%.

EXAMPLE 4

4,5-Dibromo-2-($\alpha,\alpha,\alpha$-trifluoro-p-tolyl)-pyrrole-3-carbonitrile

To a stirred mixture of 0.8 g of 2-($\alpha,\alpha,\alpha$-trifluoro-p-tolyl)pyrrole-3-carbonitrile in 70 mL of chloroform is added 2 mL of bromine. The mixture, on stirring overnight, deposits a white solid which is collected by filtration. Thin layer chromatography (1:1 ethyl acetate-hexane) shows a single component; m.p. >230° C.

Anal. Calc'd for C$_{12}$H$_5$Br$_2$F$_3$N$_2$: C, 36.55; H, 1.27; N, 7.11; Br, 40.61.
Found: C, 36.40; H, 1.08; N, 6.99; Br, 40.55.

Following the above procedure but substituting the appropriately substituted phenylpyrrole-3-carbonitrile for 2-($\alpha,\alpha,\alpha$-trifluoro-p-tolyl)pyrrole-3-carbonitrile yields the following compounds.

| L | M | R | X | Y | mp °C. |
|---|---|---|---|---|---|
| H | H | 4-NO$_2$ | Br | Br | 274–277 |
| H | H | 4-F | Cl | Cl | >220 |
| H | H | 4-F | Br | Br | >220 |

-continued

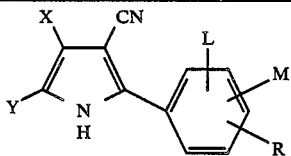

| L | M | R | X | Y | mp °C. |
|---|---|---|---|---|---|
| H | H | 4-SO$_2$CH$_3$ | Cl | Cl | >230 |
| H | 3-F | 4-F | Cl | Cl | >230 |
| H | 3-F | 4-F | Br | Br | >220 |
| 2-Cl | 3-Cl | 4-Cl | Cl | Cl | |
| 2-Br | 3-Br | 4-Br | Br | Br | |
| H | H | 4-OCF$_3$ | Cl | Cl | 222–225 |
| H | H | 4-OCF$_3$ | Br | Br | |
| H | H | 4-OCF$_3$ | Cl | H | |
| H | H | 4-CN | Br | Br | >230 |
| H | H | 4-CN | Cl | Cl | >240 |
| H | H | 4-SO$_2$CH$_3$ | Br | Br | >230 |
| H | H | 4-NO$_2$ | Cl | Cl | 246–249 |
| H | 3-Cl | 4-Cl | Br | Br | >260 |
| H | H | 3-CF$_3$ | Cl | Cl | >230 |
| H | H | 4-COCH$_3$ | Cl | Cl | 251–254 |
| H | | 2,3-CH=CH— | Cl | Cl | 244–247 |
| H | H | 4-CH$_3$ | Cl | Cl | 215–217 |
| H | 2-Cl | 4-Cl | Br | Br | >230 |
| H | H | 3-Cl | Cl | Cl | >230 |
| H | 2-Cl | 4-Cl | Cl | Cl | >230 |
| H | H | 4-Cl | Br | Br | 273–274 |
| H | H | 2-Cl | Br | Br | >230 |
| H | H | 4-CF$_3$ | Cl | Cl | >230 |
| H | H | 4-Br | Cl | Cl | >235 |
| H | H | 2-Cl | Cl | Cl | >230 |
| H | 3-Cl | 4-Cl | Cl | Cl | >235 |
| H | H | H | Cl | Cl | 254–255 |

EXAMPLE 5

α-(2,2-diethoxyethylamino)-β-nitrostyrene and 3-nitro-2-phenylpyrrole

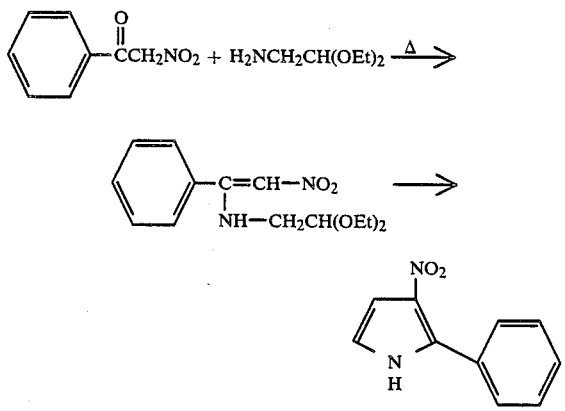

Alpha-nitro acetophenone (5.7 g, 0.0345m) is taken up in 100 mL toluene and 4.6 g (0.0345m) of amino acetaldehyde diethyl acetal is added. The reactants are put into a 250 mL RB flask fitted with a Dean-Stark trap. The trap is filled with 4A molecular sieves and the mixture is heated at reflux for 18 hours. The toluene is removed in vacuo to give 8.36 g of α-(2,2-diethoxyethylamino)-β-nitrostyrene as a brown oil. To this oil is added 50 mL of concentrated HCl. As the flask is swirled the oil turns to a yellow suspension. After 10 minutes the solid is filtered to give 2.48 g of a yellow solid. Recrystallization from ether/ethylacetate/hexane gives the product as two fractions, 2.08 g of m.p. 190°–192° C., (31%).

Max 1485 cm$^{-1}$(NO$_2$), H-NMR(CDCl$_3$/DMSO) δ6.73(m,2H), 7.46(m,5H).

Other β-nitrostyrene compounds can be prepared by the above reaction by substituting the appropriately substituted a-nitro acetophenone for α-nitro acetophenone and/or appropriate 2,2-di(C$_1$–C$_4$ alkoxy)ethylamine for amino acetaldehyde diethyl acetal to give the following compounds:

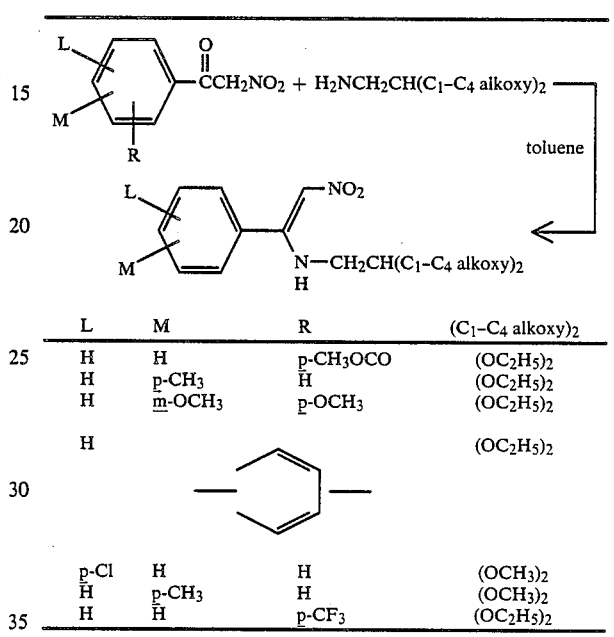

| L | M | R | (C$_1$–C$_4$ alkoxy)$_2$ |
|---|---|---|---|
| H | H | p-CH$_3$OCO | (OC$_2$H$_5$)$_2$ |
| H | p-CH$_3$ | H | (OC$_2$H$_5$)$_2$ |
| H | m-OCH$_3$ | p-OCH$_3$ | (OC$_2$H$_5$)$_2$ |
| H | | | (OC$_2$H$_5$)$_2$ |
| p-Cl | H | H | (OCH$_3$)$_2$ |
| H | p-CH$_3$ | H | (OCH$_3$)$_2$ |
| H | H | p-CF$_3$ | (OC$_2$H$_5$)$_2$ |

EXAMPLE 6

2,3-Dichloro-4-nitro-5-phenylpyrrole

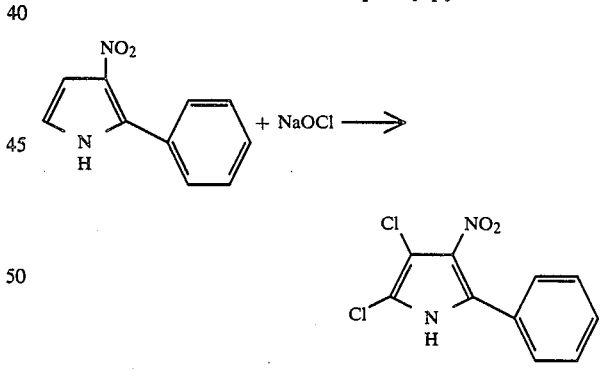

A mixture of 3-nitro-2-phenylpyrrole (1.56 g, 0.0083m) in 60 mL of dioxane is cooled in an ice bath while 25.9 g (0.0182 m) of commercial sodium hypochlorite is added dropwise. After stirring for 45 minutes, the mixture is acidified with concentrated HCl. Water and Et$_2$O are added. The layers are separated and the top organic layer is washed with H$_2$O dried over anhydrous MgSO$_4$ and concentrated in vacuo to give 2.21 g of yellow solid. Purification by chromatography using silica gel and eluting with increasing ratios of ethyl acetate/hexane gives, after stripping, 0.77 g of yellow solid (36%) m.p. 190°–190.5° C.;

Analysis: Calcd. for C$_{10}$H$_6$N$_2$O$_2$Cl$_2$C, 46.72: H, 2 35: N, 10.90.

Found: C, 46.96; H, 2.86; N, 10.02.

What is claimed is:

1. A compound having the structural formula:

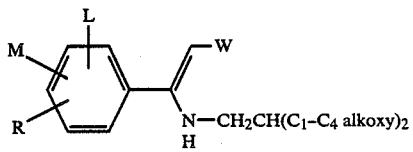

wherein W is CN or NO$_2$; L is H, F, Cl, or Br; M and R are each independently H, C$_1$-C$_3$ alkyl, C$_1$-C$_3$ alkoxy, C$_1$-C$_3$ alkylthio, C$_1$-C$_3$ alkylsulfinyl, C$_1$-C$_3$ alkylsulfonyl, cyano, F, Cl, Br, I, nitro, CF$_3$, R$_1$CF$_2$Z, R$_2$CO, or NR$_3$R$_4$ and when on adjacent positions and taken together with the carbon atoms to which they are attached M and R may form a ring in which MR represent the structure: —OCH$_2$O—, —OCF$_2$O— or

Z is SO$_n$ or O; R$_1$ is H, F, CHF$_2$, CHFCl, or CF$_3$; R$_2$ is C$_1$-C$_3$ alkyl, C$_1$-C$_3$ alkoxy, or NR$_3$R$_4$; R$_3$ is H or C$_1$-C$_3$ alkyl; R$_4$ is H, C$_1$-C$_3$ alkyl, or R$_5$CO; R$_5$ is H or C$_1$-C$_3$ alkyl; and n is an integer equal to 0, 1 or 2.

2. A compound according to claim 1, (E) p-chloro-β-[(formylmethyl)amino]cinnamonitrile diethyl acetal.

3. A compound according to claim I, (Z) p-chloro-β-[(formylmethyl)amino]cinnamonitrile diethyl acetal.

4. A compound according to claim 1, β-[(formylmethyl)amino]-3,4-dimethoxycinnamonitrile diethyl acetal.

5. A compound according to claim 1, (Z)-methyl p-{2-cyano-1-[(formylmethyl)amino]vinyl}benzoic acid diethyl acetal.

6. A compound according to claim 1, 3,4-dichloro-β[(formylmethyl)amino]cinnamonitrile diethyl acetal.

7. A compound according to claim 1, (Z)-β-[(formylmethyl)amino]-p-methylcinnamonitrile diethyl acetal.

8. A compound according to claim 1, β-[(formylmethyl)amino]p-trifluoromethoxycinnamonitrile dimethyl acetal.

9. A compound according to claim 1, (E) p-chloro-β-[(formylmethyl)amino]cinnamonitrile dimethyl acetal.

10. A compound according to claim 1, N-(formylmethyl)-p-methyl-α-(nitromethylene)benzylamine diethyl acetal.

11. A compound according to claim 1, N-(formylmethyl)-3,4-dimethoxy-α-(nitromethylene)benzylamine diethyl acetal.

12. A compound according to claim 1, p-chloro-N-(formylmethyl)-α-(nitromethylene)benzylamine diethyl acetal.

13. A compound according to claim 1, N-(formylmethyl)-α-(nitromethylene)-2-naphthenemethylamine diethyl acetal.

14. A compound according to claim 1, methyl p-{α-[(formylmethyl)amino]-β-nitrovinyl}benzoate p-(diethylacetal).

15. A compound according to claim 1, p-trifluoromethyl-N-[formylmethyl-α-(nitromethylene)]-benzylamine diethyl acetal.

16. A process for the preparation of a compound represented by the structure:

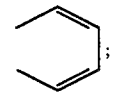

wherein W is CN or NO$_2$ L is H, F, Cl, or Br: M and R are each independently H, C$_1$-C$_3$ alkyl, C$_1$-C$_3$ alkoxy, C$_1$-C$_3$ alkylthio, C$_1$-C$_3$ alkylsulfinyl, C$_1$-C$_3$ alkylsulfonyl, cyano, F, Cl, Br, I, nitro, CF$_3$, R$_1$CF$_2$Z, R$_2$CO, or NR$_3$R$_4$ and when on adjacent positions and taken together with the carbon atoms to which they are attached M and R may form a ring in which MR represent the structure: —OCH$_2$O—, —OCF$_2$O— or

Z is SO$_n$ or O; R$_1$ is H, f, CHF$_2$, CHFCl, or CF$_3$; R$_2$ is C$_1$-C$_3$ alkyl, C$_1$-C$_3$ alkoxy, or NR$_3$R$_4$; R$_3$ is H or C$_1$-C$_3$ alkyl; R$_4$ is H, C$_1$-C$_3$ alkyl, or R$_5$CO; R$_5$ is H or C$_1$-C$_3$ alkyl; and n is an integer equal to 0, 1, or 2; comprising, reacting a benzoylacetonitrile or α-nitroacetophenone having the structure:

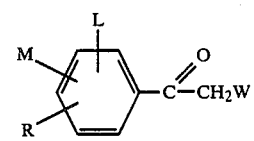

wherein L, M, R, and W are as described above with 2,2-di(C$_1$-C$_4$ alkoxy)ethylamine, at an elevated temperature, to give a compound having the structure:

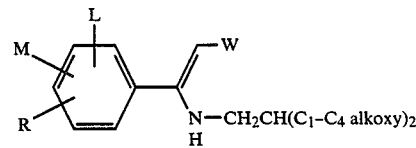

wherein L, M, R, and W are as described above.

* * * * *